United States Patent [19]
Portwood et al.

[11] Patent Number: 5,950,630
[45] Date of Patent: Sep. 14, 1999

[54] SYSTEM AND METHOD FOR IMPROVING COMPLIANCE OF A MEDICAL REGIMEN

[76] Inventors: Michael T. Portwood, 1091 Plains—Port Hudson Rd., Zachary, La. 70791; John W. Portwood, 10243 Winterhue Dr., Baton Rouge, La. 70810

[21] Appl. No.: 08/766,584

[22] Filed: Dec. 12, 1996

[51] Int. Cl.$^6$ .................................................. A61B 19/00
[52] U.S. Cl. .......................... 128/897; 128/904; 128/906; 364/400; 705/2; 705/3
[58] Field of Search .................................. 128/904, 906, 128/897; 364/400; 705/2, 3

[56] References Cited

U.S. PATENT DOCUMENTS

| | | | |
|---|---|---|---|
| 4,695,954 | 9/1987 | Rose et al. | 364/413 |
| 4,766,542 | 8/1988 | Pilarczyk | 364/413 |
| 4,831,562 | 5/1989 | McIntosh et al. | 364/569 |
| 4,838,275 | 6/1989 | Lee | 128/670 |
| 4,913,083 | 4/1990 | Valvo et al. | 116/308 |
| 4,958,280 | 9/1990 | Paul et al. | 705/3 |
| 5,319,335 | 6/1994 | Russek | 340/573 |
| 5,390,238 | 2/1995 | Kirk et al. | 379/93 |

OTHER PUBLICATIONS

Leirer et al *The Gerontologist*, vol. 31, No. 4, 514–520, 1991 "Elders'Nonadherence; Its Assessment and Medication Reminding by Voice Mail".

Venter et al SAMJ, vol. 79, May 4, 1991 "Compliance in Black Patients with Non–insul in Dependent Diabetes Mellitus Receiving Oral Hypoglycaemic Therapy".

De Geest et al *Transplantation*, vol. 59, 340–347, Feb. 15, 1995 "Incidence, Determinants, and Consequences of Sub–clinical Noncompliance with Immunosuppressive Therapy in Renal Transplant Recipients".

Buchanan *Seizure*, vol. 2, 79–82, 1993 "Noncompliance with Medication Amongst Persons Attending a Tertiary Referral Epilepsy Clinic: Implications, Management and Outcome".

Clark *American Heart Journal*, 664–669, Feb. 1991 "Improving Compliance and Increasing Control of Hypertension: Needs of Special Hypertensive Populations".

Bittar *Clinical Cardiologist*, vol. 18 (Suppl. III), III–12–III–16 (1995) "Maintaining Long–Term Control of Blood Pressure: The Role of Improved Compliance".

Kjellgren et al *International Journal Of Cardiology*, vol. 47, 257–268 (1995) "Taking Antihypertensive Medication—Controlling or Co–operating with Patients?".

Monane, et al *Arch Intern Med*, vol. 154, 433–437 (1994) "Noncompliance with CongestiveHeart Failure Therapy in the Elderly".

(List continued on next page.)

*Primary Examiner*—Linda C.M. Dvorak
*Assistant Examiner*—Rosiland Kearney
*Attorney, Agent, or Firm*—Roy, Kiesel & Tucker

[57] ABSTRACT

A system and method for improving compliance by a patient with a medical regimen that has been prescribed to the patient wherein utilizing computer and electronic communication systems, patient data is compared to pharmaceutical data to verify prescribed drug dosage and prescribed medication duration are within acceptable limits, any abnormalities found by the comparisons are reported to the treating physician who may then alter the medical regimen before authorizing dispensing of the prescribed drugs and providing drug taking information to the patient, and upon authorization being issued, the patient is scheduled to receive reminder notifications prior to the prescribed time for the prescribed drugs to be administered, as well as automatically notifying the prescription distribution service to deliver the prescribed drugs to the patient, and notifying the payor service to pay for the prescribed drugs.

20 Claims, 13 Drawing Sheets

OTHER PUBLICATIONS

Sclar *Clinical Therapeutics*, vol. 13, No. 4, 436–440 1991 "Improving Medication Compliance: A Review of Selected Issues".

Raynor et al *BMJ*, vol. 306, 1158–61, 1993 "Effects of Computer Generated Reminder Charts on Patients'Compliance with Drug Regimens".

Salzman *J Clin Psychiatry*, vol. 56 (suppl 1), 18–22 1995 "Medication Compliance in the Elderly".

Col et al *Arch Intern Med*, vol. 150 Apr. 1990 "The Role of Medication Noncompliance and Adverse Drug Reactions in Hospitalizations of the Elderly".

Colley et al *Journal Of General Internal Medicine*, vol. 8, 278–283, May 1993 "Polypharmcy: The Cure Becomes the Disease".

Gravely et al *Research In Nursing & Health*, vol. 14, 51–58, 1991 "Multiple Drug Regimens: Medication Compliance Among Veterans 65 Years and Older".

Botelho et al *The Journal Of Family Practice*, vol. 35, No. 1, 1992 "Home Assessment of Adherence to Long–term Medication in the Elderly".

Einarson *The Annals Of Pharmaco–Therapy*, vol. 27, Jul./Aug. 1993 "Drug–related Hospital Admissions".

Lamy *MMJ*, vol. 38, No. 2, 144–148, Feb. 1989 "Pharmacotherapeutics in the Elderly".

Fitten et al *Journal Of American Geriatrics Society*, vol. 43, 361–367, 1995 "Assessment of Capacity to Comply with Medication Regimens in Older Patients".

SYSTEM AND METHOD FOR IMPROVING COMPLIANCE OF A MEDICAL REGIMEN

BACKGROUND OF THE INVENTION

1. Field of the Invention

This invention relates in general to a system and method to facilitate compliance with a prescribed medical regimen and ensure integrity of the prescribed medical regimen, and more particularly, to a system and method to monitor the patient usage of drugs prescribed by the patient's physician and to verify that a prescription meets reasonable standards for the drug involved.

2. Prior Art

Noncompliance with a prescribed medical regimen, especially the inaccurate use of prescription drugs, is one of the main reasons for most outpatient treatment failure, as well as a cause of serious, life threatening medical complications.

The seriousness of the problem has been long recognized by the medical community. Numerous studies have been undertaken in an effort to identify the causes of noncompliance of a medication regimen. Various causes identified by these studies include forgetfulness, number of medications prescribed, unclear instructions or a lack of written instructions, side effects of the medication, cost of the medication, inconvenient or complex dosing schedules, lack of a primary health care physician, or lack of prescribed medication information given by the primary health care physician.

In attempts to overcome one or more of these causes, various equipment and systems have been devised. Examples of such systems can be seen in U.S. Pat. No. 4,695,954 which combines a special drug dispenser to be used by a patient in conjunction with a system which monitors the usage of the drugs by the patient. Another system is disclosed in U.S. Pat. No. 4,766,542 wherein patients are automatically contacted by automatic telephone dialing and voice synthesizing equipment to remind them that their prescriptions need to be refilled. U.S. Pat. No. 5,390,238 discloses a system linking the physician, pharmacists, patient, and care provider for the purpose of monitoring medication usage and patient wellness. However, the various prior art systems have proven to be workable only in controlled environments. Even then they leave unsolved many of the numerous other causes of noncompliance.

A second problem relating to medical regimens is lack of easy checking procedures to determine if a prescription complies with a recommended regimen. Currently, the U.S. FDA publishes a Generic Product Identifier (GPI) which is a listing of available drugs coded by their generic chemical composition and a National Drug Code (NDC) which is a listing of available drugs coded by their trade names. However, neither the GPI nor the NDC contain drug reaction information. There does exist a collection of studies which describe known reactions for certain drugs. This collection of studies is referred to herein as the Knowledge Base Drug Code (KDC). In addition, there are other studies which have established classes based on composition of the components which make up a drug. However, a compilation of this available information has not been assembled for easy use.

Thus, there remains in the medical community the need for a system, and a method of using the system, that better ensures that a treating physician will be aware of all medications that a patient may be taking, that informs the treating physician of possible drug interactions or drug dosage and administering duration that are outside of recommended ranges, that permits contacting the patient when his medication is due regardless of where the patient may be located at that moment, that assists the treating physician in prescribing not only the best medication, but also a dosage and duration that is within recommended ranges, as well as a system that streamlines the number of medications that the patient is taking, and that incorporates automatic mail ordering, billing, and other business aspects of prescribing a medical regimen.

OBJECTS AND SUMMARY OF THE INVENTION

Therefore, one object of this invention is to provide a system which better addresses the causes contributing to the inaccurate use of prescription drugs and reducing noncompliance by a patient of the medical regimen prescribed for the patient.

Another object of this invention is to provide a system that identifies for the treating physician possible dosing, administering duration, or drug interaction problems that might result from a prescribed medication regimen.

Another object of this invention is to provide a system that has the ability to assist the treating physician in prescribing the best medical regimen for the patient and not merely the most convenient.

A further object of this invention is to provide a system that enables the treating physician to streamline the number of medications in a medical regimen, as well as to reduce polypharmacy problems.

Still another object of this invention is to provide a system that has the ability to contact mobile patients no matter where they may be located at a particular time.

A still further object of this invention is to provide a system that has the ability to contact mobile patients when their medication is due and not after the fact.

Another further object of this invention is to provide a system that has the ability to timely remind patients to refill prescriptions.

Another object of this invention is to provide a system that assists in the ordering of prescription refills in a manner that reduces costs to the entity paying for the prescriptions.

A still further object of this invention is to provide a system that can generate reports useful to the treating physician, the patient, the medication provider, and the medication regimen payment source.

Another object of this invention is to provide a system that assists in improving the communication between the treating physician and the patient, in notifying the patient of upcoming appointments, and in specifying procedures in the medical regimen that the patient should follow.

Other objects and advantages of the invention will become apparent from the ensuing descriptions of the invention.

Accordingly, a system to facilitate compliance with a prescribed medical regimen is provided, which comprises a computer system having a data storage unit containing stored pharmaceutical data, a central processing unit (CPU) programmed and operatively connected to the data storage unit to further store in the data storage unit patient data and patient prescription data, and an inputting unit operatively connected to the CPU to transmit patient data and patient prescription data to the CPU, and a reporting unit operatively connected to the CPU; the CPU being further programmed to compare the patient data, the patient prescription data, and the pharmaceutical data to determine if the patient prescription data is within an acceptable medication dosage range as defined by the pharmaceutical data, and to transmit the determination to the reporting unit.

In a preferred embodiment of the invention, the CPU is further programmed to compare the patient data, the patient prescription data and the pharmaceutical data to determine if the patient prescription data is within an acceptable medication administering duration range as defined by the pharmaceutical data, and to transmit the determination to the reporting unit.

In another preferred embodiment of the invention, the CPU is further programmed to compare the patient data, the patient prescription data and the pharmaceutical data to determine if the patient prescription data is within an acceptable medication maintenance dosage or within an acceptable medication acute dosage range as defined by the pharmaceutical data, and to transmit the determination to the reporting unit.

In still another preferred embodiment of the invention, the CPU is further programmed to generate from approved patient prescription data a patient message, and wherein the system further comprises a message receiving unit operatively connected to the CPU to receive the patient message from the CPU. In a more preferred embodiment, the message receiving unit will comprise a modem operatively connected to a transmission unit which can transmit the patient message to a pager.

In still another preferred embodiment of the invention, the CPU is further programmed to generate a prescription delivery message, and wherein the system further comprises a message receiving unit operatively connected to the CPU to receive the prescription delivery message from the CPU.

In a further preferred embodiment of the invention, the system comprises two or more linked computer systems. One computer system is the server computer station and the other computer systems are prescriber computer systems. The server computer station will serve as the repository of the data bases used by each of the prescriber computer systems and will deliver that portion of the data bases requested by one of the prescriber computer stations. Each prescriber computer station shall then process the information provided by the server computer station, as well as information which it may have stored in its own data base storage unit, in accordance with instructions set forth in its operating program. The prescriber computer station will be further provided with one or more communication units, such as a modem, for transmitting messages, including prescription orders, determined by the results of the processed information to the server computer station. The server computer station upon receipt of these messages, and in accordance with its operating program, will timely transmit these messages to pre-determined parties.

BRIEF DESCRIPTION OF THE DRAWINGS

The specification and the accompanying drawings show and describe a preferred embodiment of this invention, but it is to be understood that this embodiment is not intended to be exhaustive nor limiting of the invention, but on the contrary is given for the purpose of illustration in order that others skilled in the art may fully understand the invention and the principles thereof and the manner of applying it in practical use so that they may modify and adapt it in various forms, each as may be best suited to the conditions of a particular use.

FIG. 3A-1 is a schematic of a preferred embodiment of the subroutine of the computer software architecture utilized by the system to determine if the prescribed drug regimen is within the recommended daily and unit drug dosage ranges.

FIG. 3A-2 is a schematic of a preferred embodiment of the subroutine of the computer software architecture utilized by the system to determine if the prescribed drug regimen is within the recommended drug duration range.

PREFERRED EMBODIMENTS OF THE INVENTION

Although it is within the scope of this invention that each prescriber could be equipped with a computer system that would perform all of the functions discussed below, the preferred system includes a central server computer system A to which will be operatively connected to one or more prescriber computer systems B. In this preferred embodiment the central processing units (CPUs) of each computer system will be programmed to perform separate tasks. In the stand alone system, the CPU of the prescriber will be programmed to perform all of the separate tasks. It is also within the scope of this invention that the tasks to be performed could be achieved by either the server CPU or the prescriber CPU through well known and easy to perform programming changes. It is also within the scope of this invention that the retention of the various types of data maintained by the system could be retained either in the internal hard drives of the server computer system A or the prescriber computer system B, or in external memory units operatively attached to either, or through the use of other known data storage media.

The Computer Hardware Utilized in the Preferred System

Figure 1:
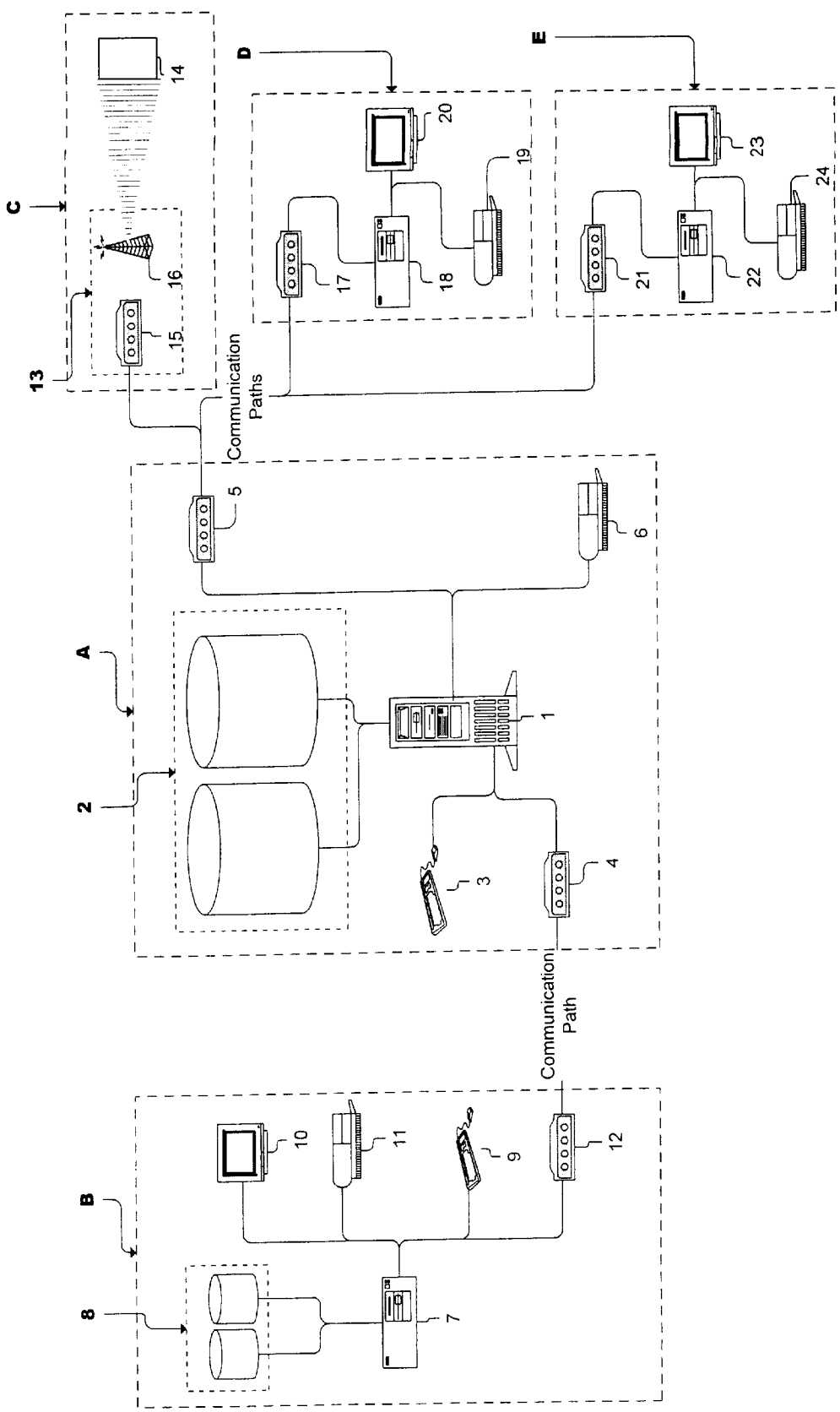
FIG. 1 is schematic of an overview of a preferred embodiment of the system of this invention.

It is seen from FIG. 1 that in the preferred embodiment of the invention, the system comprises a server computer station A, and a prescriber computer station B which are programmed to provide drug dosage, administering duration, drug interaction and patient drug reaction checks from the data stored in the two stations. In a more preferred embodiment, the system will also comprise a patient message receiving system C through which the patient can be timely reminded to take the medication contained in the medical regimen. In another more preferred embodiment, the system will also comprise a prescription distribution system D that enables quicker initial delivery and which better ensures timely refills of prescriptions. In still another more preferred embodiment, the system may also comprise an invoice payment system E that expedites payment, and reduces payment processing costs. With the equipment contained in each system, each of the communications graphically depicted in FIG. 2, and discussed below, is made possible.

In the most preferred embodiment, the server computer station A comprises a central processing unit (CPU) 1; a data storage unit, such as a disc and/or hard drive 2, for storing patient data, patient prescription data, pharmaceutical data and the CPU's operating programs; a data input unit, such as a keyboard 3, for inputting data or operating instructions into CPU 1; one or more communication units, such as modems 4 and 5, for transmitting data or messages to the prescriber computer station B or the patient message receiving system C; and a printer 6 for preparing hard copies of invoices or reports generated by the server CPU 1 or the prescriber computer station B. Each of the elements making up the server computer station A are operatively connected to one another by well known means, such as hard wiring, telephone lines, microwave transmission means, and similar devices, to permit the functions which each element normally performs.

The prescriber computer station B comprises a central processing unit (CPU) 7; a data storage unit, such as a CD and/or hard drive 8, for storing patient and patient medical regimen data, and the CPU's operating programs; a data input unit, such as keyboard 9, for inputting data or operating instructions into CPU 7; an audio speaker or video monitor 10; a printer 11; and a communication unit, such as modem 12, for transmitting data to and receiving data from the server computer station A. Similar to server computer station A, each of the elements making up the prescriber computer station B are also operatively connected to one another by well known means to permit the functions which each element normally performs.

In a preferred embodiment, the patient message unit C comprises a message receiving and sending means 13 and a pager 14, and more preferably a two-way pager. Means 13 will include a modem 15 and a pager transmitting unit 16. In a more preferred embodiment pager 14 is a two-way pager to permit the patient to confirm receipt of the message, as well as respond to any queries contained in the message. Such inquiries may include questions related to the health of the patient. Other known two-way communication systems may also be used.

In a preferred embodiment, the prescription distribution system D includes a modem 17 and a CPU 18 for receiving the information and transcribing this information in a format that enables one to prepare the medication prescribed by the physician. In a more preferred embodiment, the prescription distribution system D will also comprise a reporting unit, such as printer 19 and CRT monitor 20, which permits viewing of the billing statement and subsequent printing of a hard copy of the billing statement that is to be transmitted to the payor of the medication delivered to the patient. The payor may be the patient, a HMO, other health maintenance provider, or government agency.

In a preferred embodiment, the invoice payment system E will include a computer system, including modem 21 operatively connected to the prescription distribution system D to receive a billing statement for the medication prescribed, a CPU 22 to process the information contained in the billing statement, as well as a CRT monitor 23 and printer 24 to view and print checks, as well as other information. As reflected in FIGS. 1 and 2, this information can utilize the server system A as a conduit for transmitting the billing statement. If server system A is provided with a data base containing the payor identification and drug cost charged by the prescription delivery service D, then server system A can directly generate and transmit the billing statement to the payment system E.

Alternatively, the prescription delivery system D and the payor system E could be directly linked by computers to transmit the billing statement and to make payments directly to the prescription delivery system D.

It is within the scope of this invention that for each of the computer elements used in the server computer station A, the prescriber computer station B, the patient message unit C, the prescription distribution system D, or the payment system E, devices which perform the same function, or which perform one or more of the functions described, could be substituted for the preferred computer element, or elements. As an example, a voice recognition system could be substituted for the keyboards 3 or 9. Another example would include the substitution of a speaker system for the monitors 10, 20, or 23. A still further example would include the use of separate database storage units such as tape systems for the hard drives 2 or 8. The particular computer hardware that is used is not critical. It is important, however, that there be a computer element present to perform the desired function.

The Communications Amongst Users of the System

Figure 2:
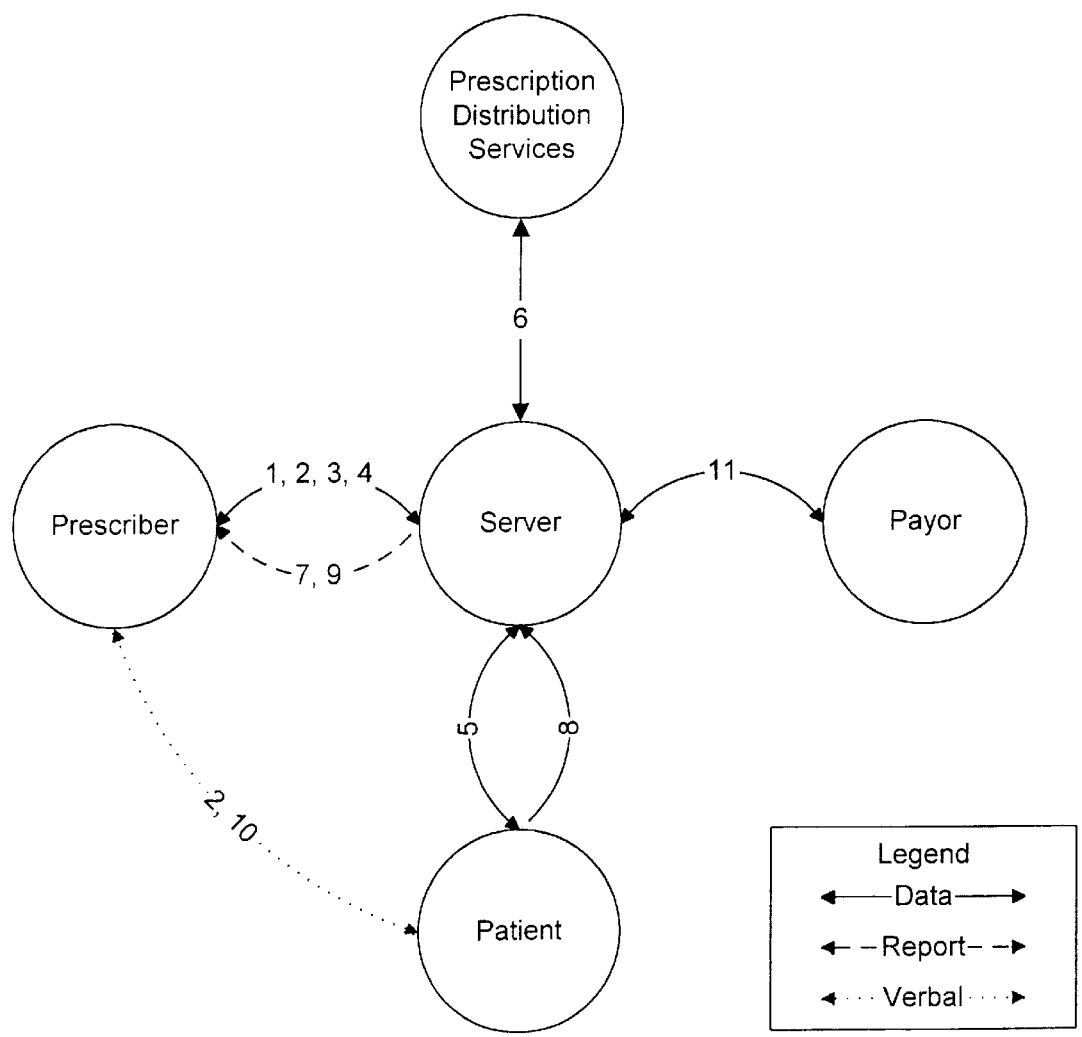
FIG. 2 is a schematic of a preferred embodiment of the system that illustrates the flow of data, reports, and verbal communication within the system and method of use of the system.

FIG. 2 illustrates an overview of a preferred use of the server computer station A to obtain a preferred flow of data, reports, and messages amongst the physician, the prescription distribution service organization, the patient, and the prescription payor. The various channels of information flow are described below as indicated by the information flow numbers in FIG. 2.

1. The prescriber utilizing the prescriber computer station B enters information about the patient that is then transmitted to the server computer station A. If the patient is currently being prescribed by another prescriber in the system, or has been prescribed in the past by a prescriber in the system, the patient's billing, medical, and prescription history will already exist within the server data base Unit 2. This information will be communicated to the prescriber computer station B.

2. The patient is assigned a pager 14. If the patient already has pager 14 the assignment is not necessary.

3. Prescription information for the patient is entered into the system by the prescriber. This information includes, but is not limited to, drug name, units and strength, prescription signature, refills, dosing mode, and a date and time that the first dose is to be administered. Pharmaceutical information related to the drugs being prescribed is transmitted from the server computer station A to the prescriber computer system B. There the pharmaceutical information is compared to the patient data and patient prescription data to ascertain if the drug regimen is within recommended ranges and to determine if any drug interaction problems exist. These include a series of tests performed on the prescription to see if it may have adverse effects. These tests include, but are not limited to underdosing, overdosing, length of therapy, drug—drug interactions, drug-food interactions, drug-alcohol interactions, and prior adverse reactions. Any of these circumstances will be reported to the person, such as the treating physician, entering the prescription information, where an appropriate action can be taken.

4. Once the drug regimen has been finalized, the prescription data is transferred to the server for validation, certification, and distribution.

5. Messages are scheduled for distribution to the patient via the patient message receiving system C. This schedule can easily be changed by the prescriber through the system.

6. Prescriptions can be distributed to a prescription distribution company, such as a pharmacy, or drug wholesale company, and in turn the distribution company can, via the server, invoice the payor (see 11 below).

7. Patient reporting may be provided, including but not limited to, general information, prescription history, and prescription calendar. This reporting would be made to the prescriber via the server, or could be made directly to the prescriber.

8. Responses to the messages are received from the patient and recorded for reporting to the prescriber.

9. Compliance information is reported to the prescriber. This type of reporting is available only if the patient message receiving system C is capable of providing an answer back capability, such as may be provided by a two-way pager.

10. Changes to the prescription including drug, time and date of treatments, etc. are communicated to the prescriber. All changes are initiated by the prescriber, who can make the changes via the steps described above.

11. Billing and other communications can be made with the prescription payor.

The Method of Utilizing the System for Medical Regimen Integrity

Figure 3:
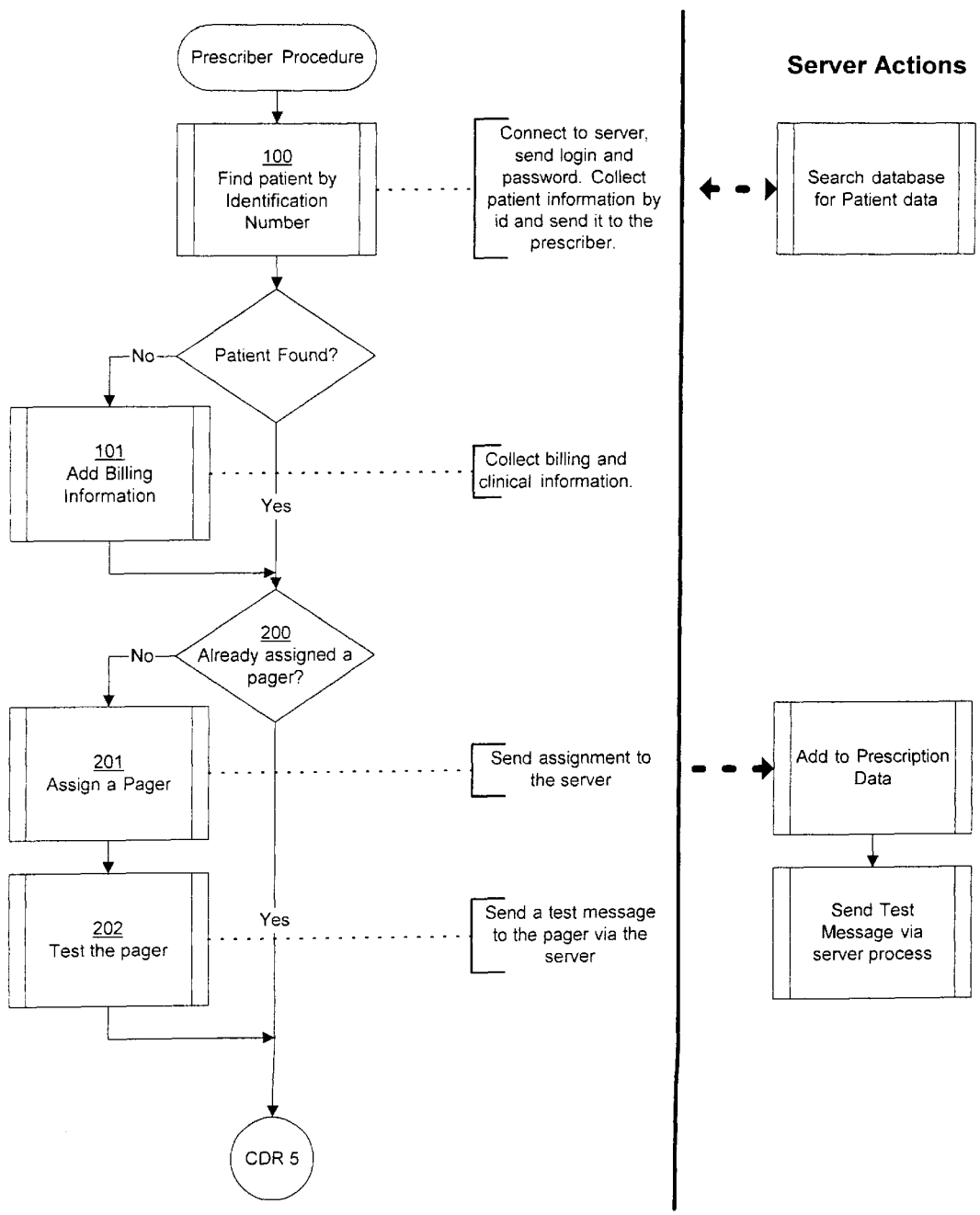
FIG. 3 is a schematic of a preferred embodiment of the computer software architecture utilized by the system and the method of use of the system detailing the steps taken by the physician and the reports generated by the system.
Figure 3:
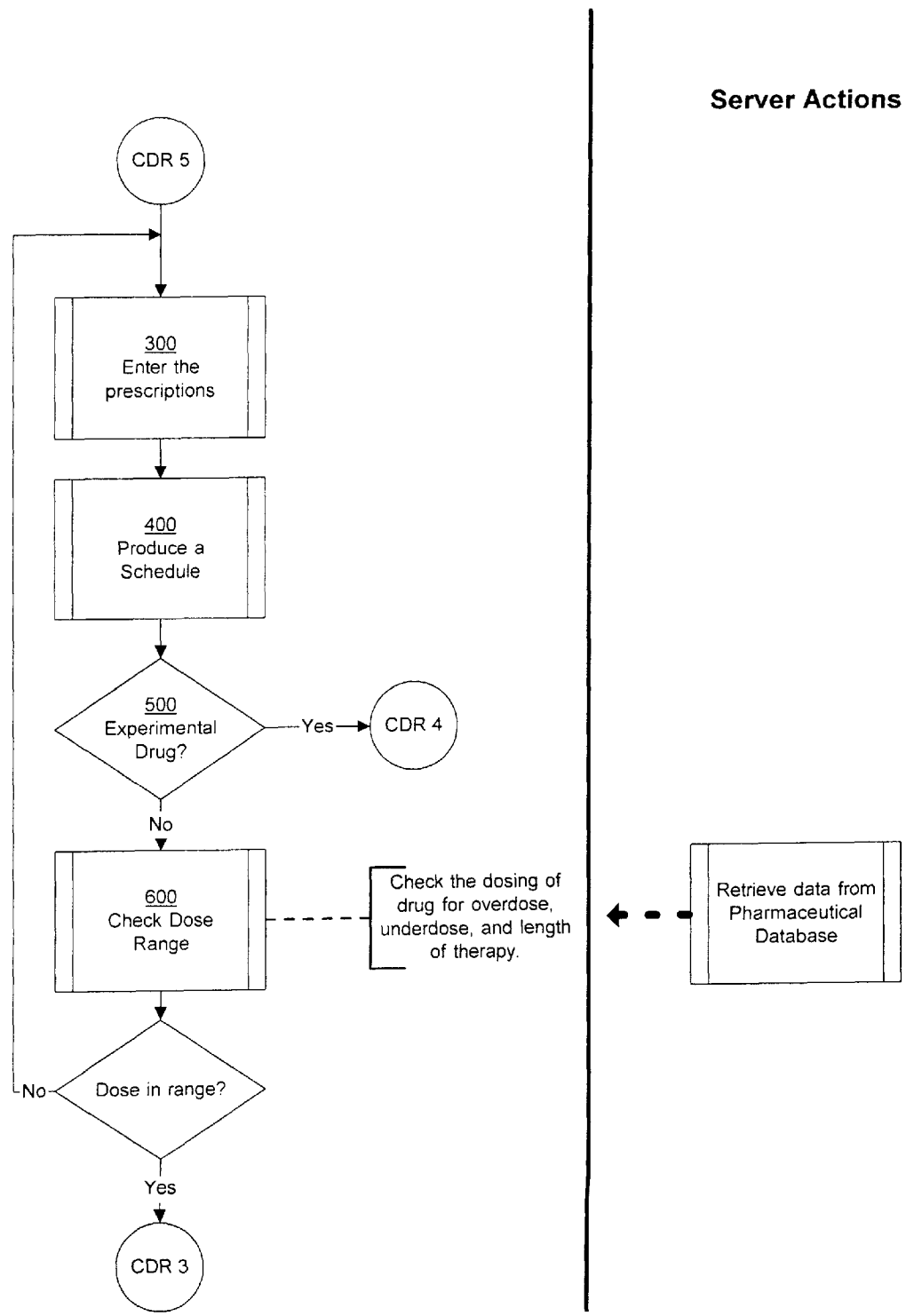
Figure 3:
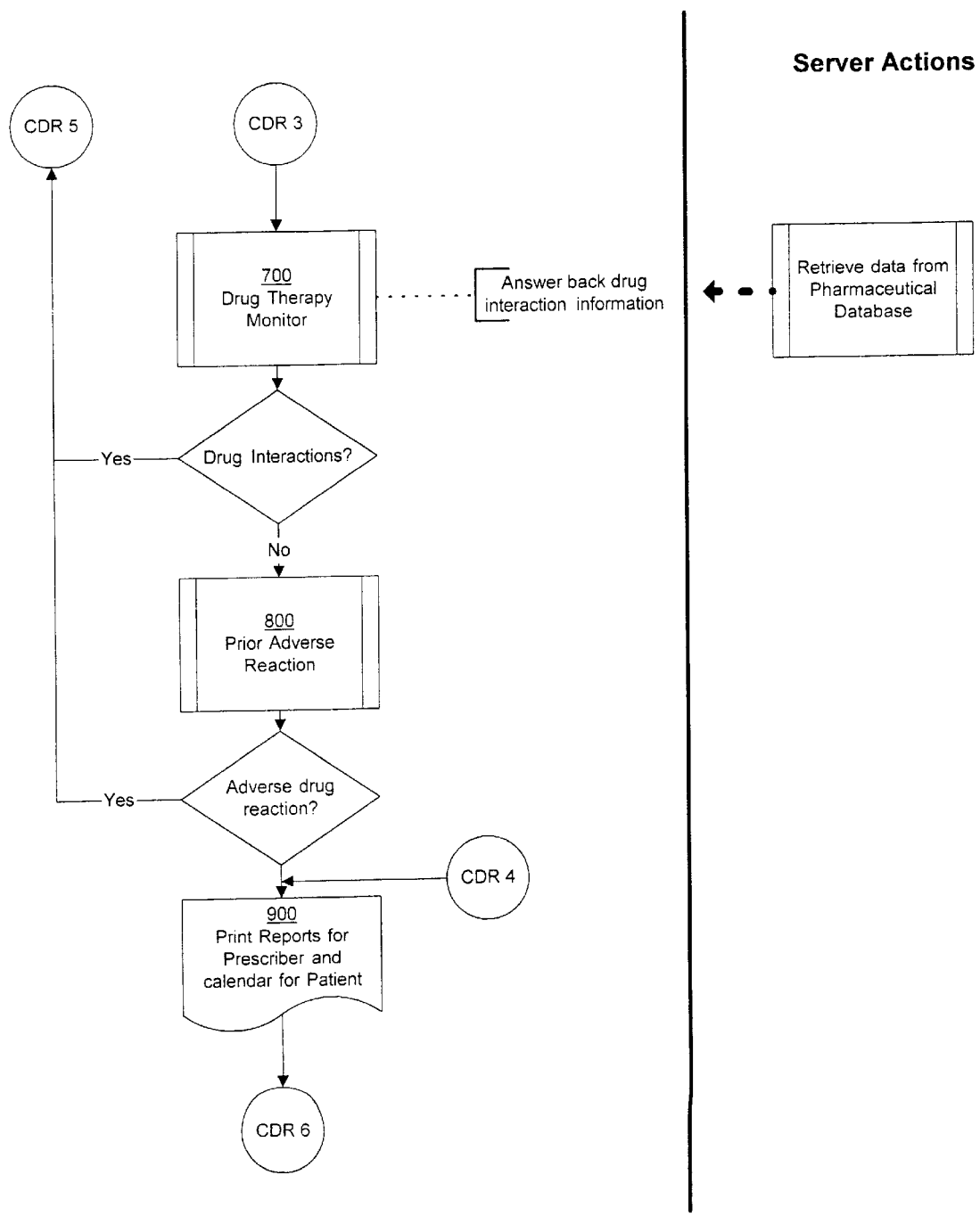
Figure 3:
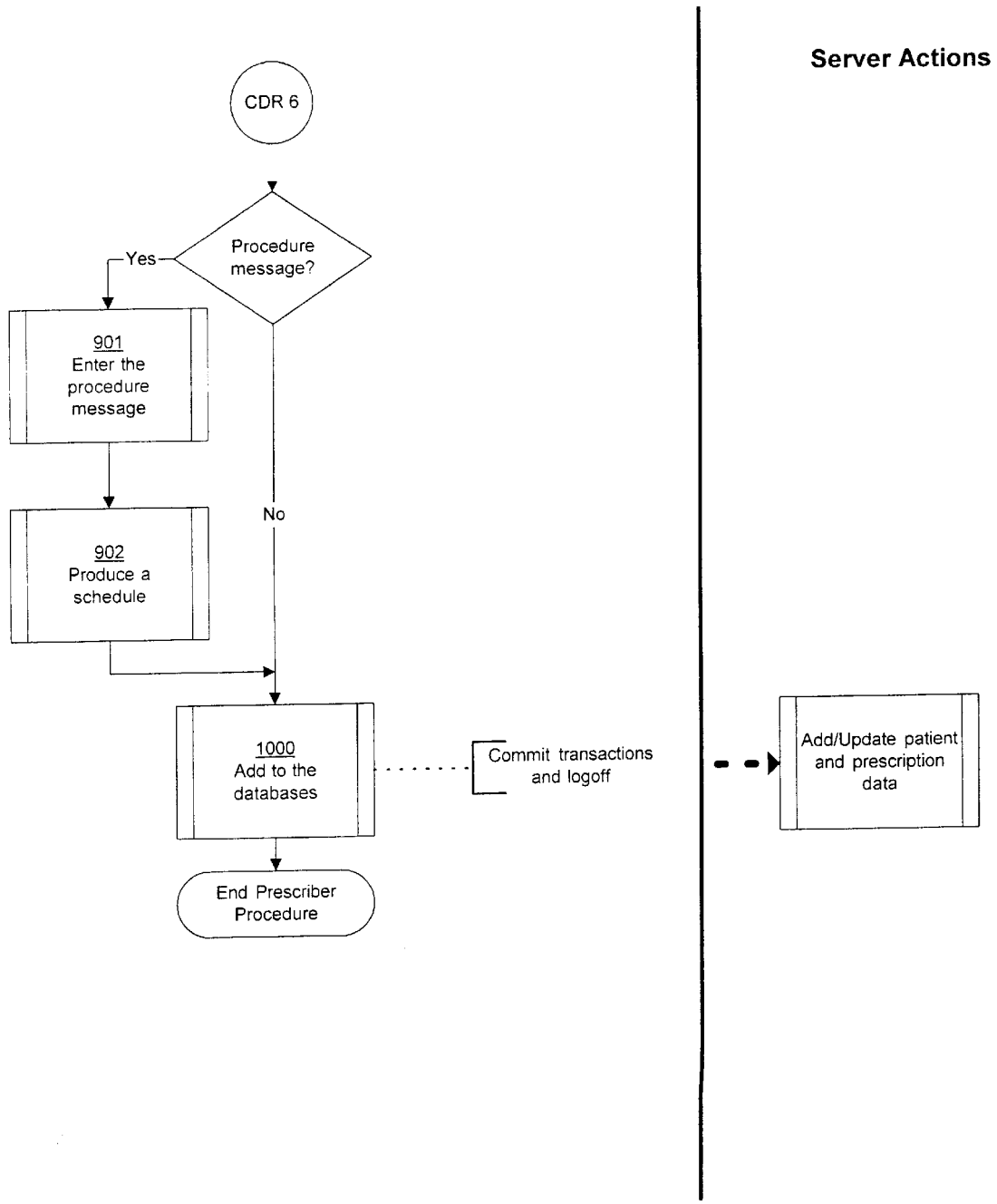
Figure 3A:
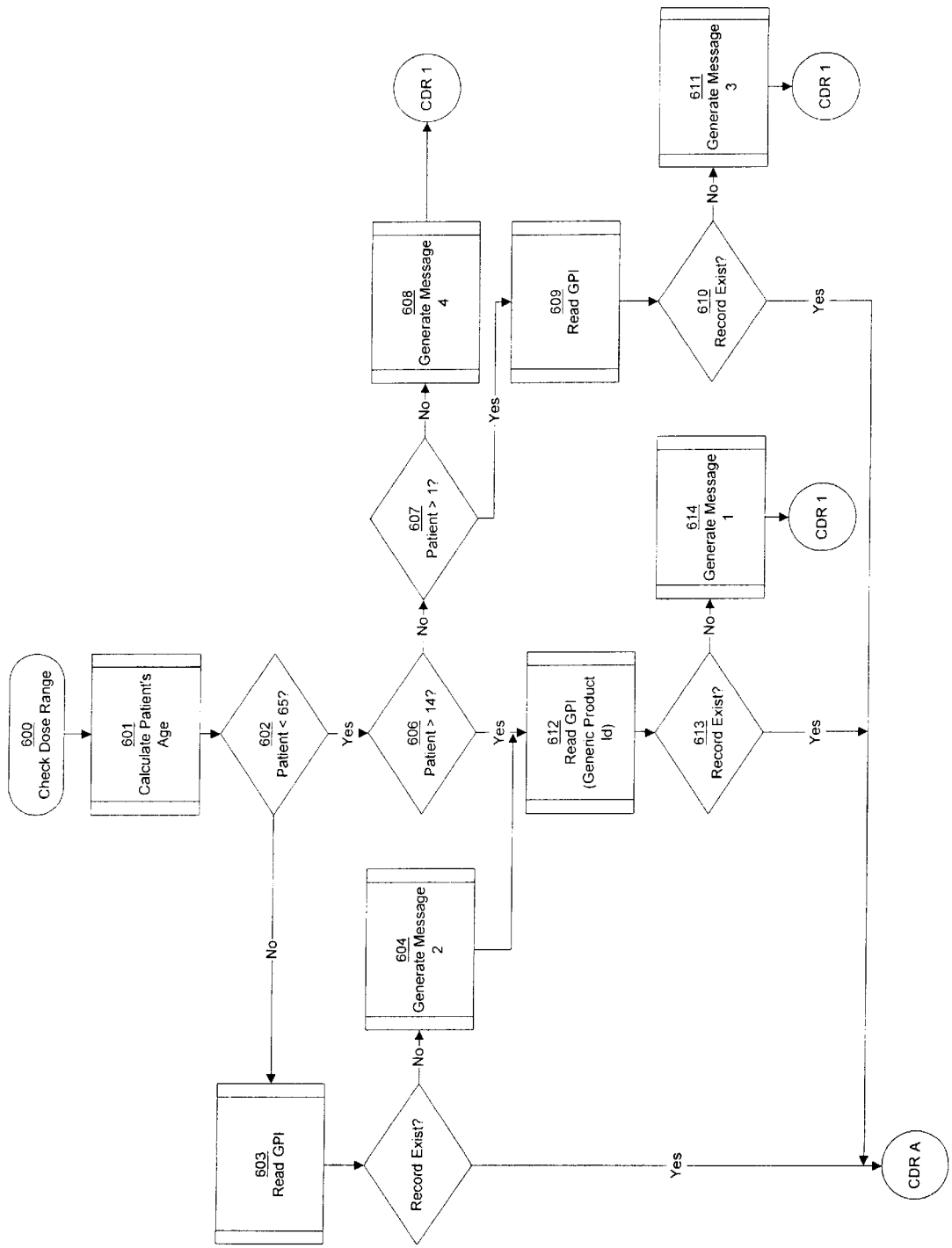
FIG. 3A is a schematic of a preferred embodiment of the computer software architecture utilized by the system to check the drug dosing for over dose, under dose, and length of therapy.
Figure 3A:
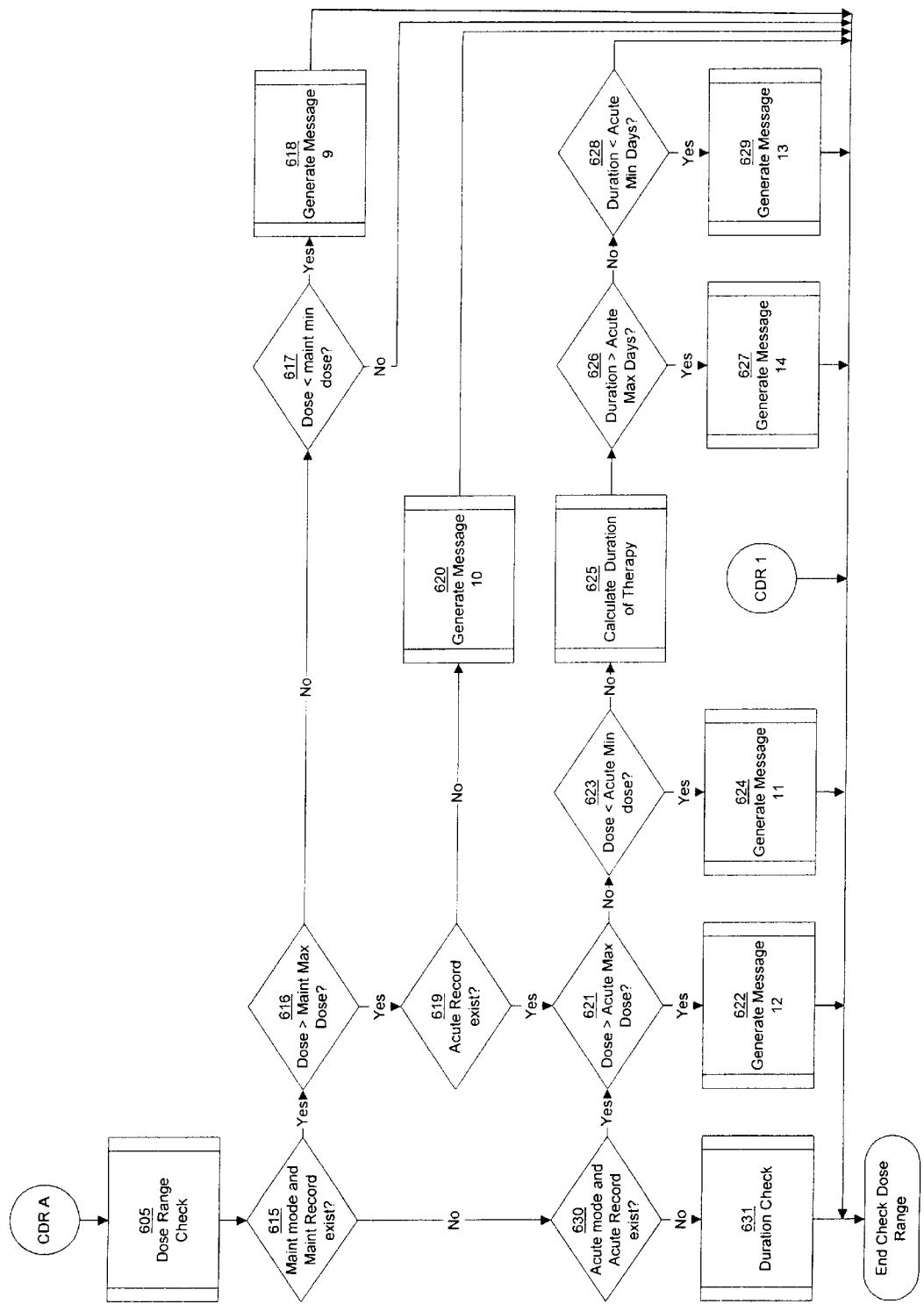
Figures 1, 3A:
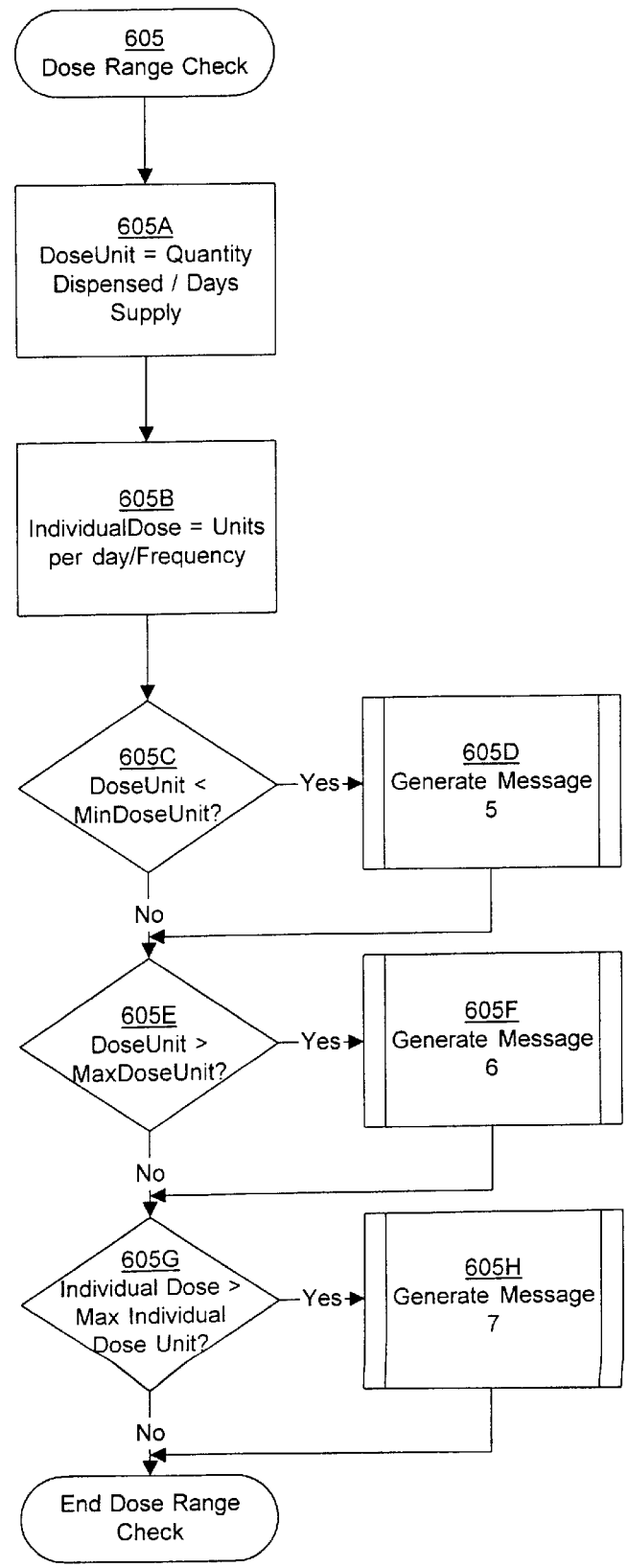
Figures 2, 3A:
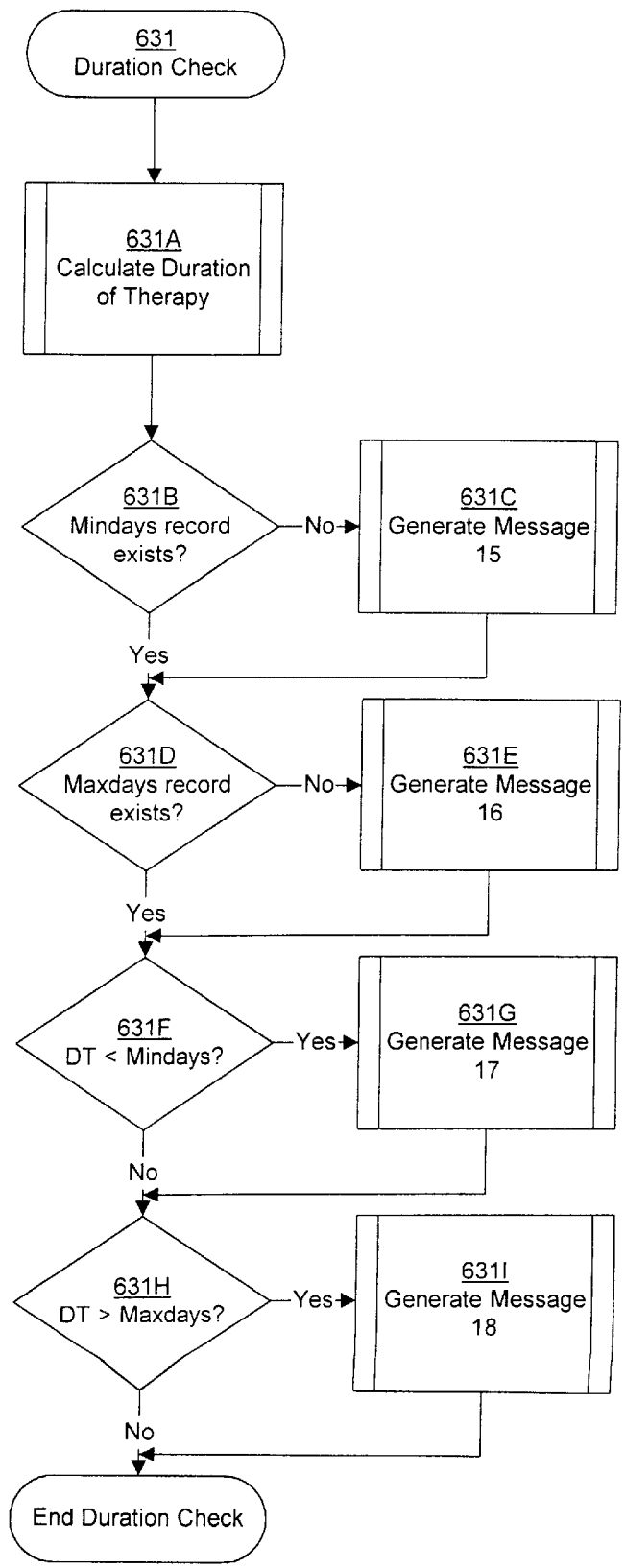
Figure 3B:
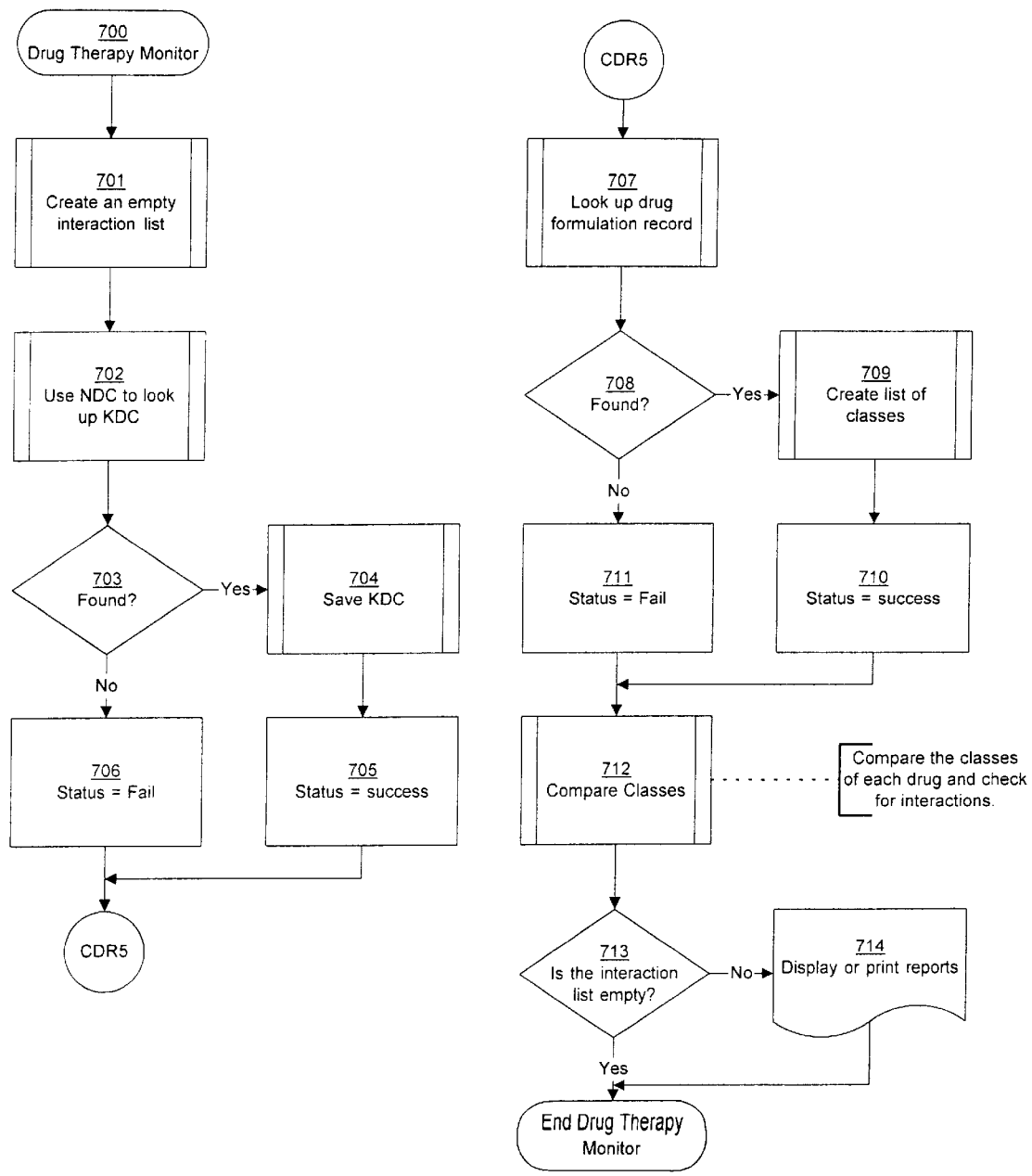
FIG. 3B is a schematic of a preferred embodiment of the computer software architecture utilized by the system to check for adverse drug interactions among the drugs included in the patient medical regimen.
Figure 4:
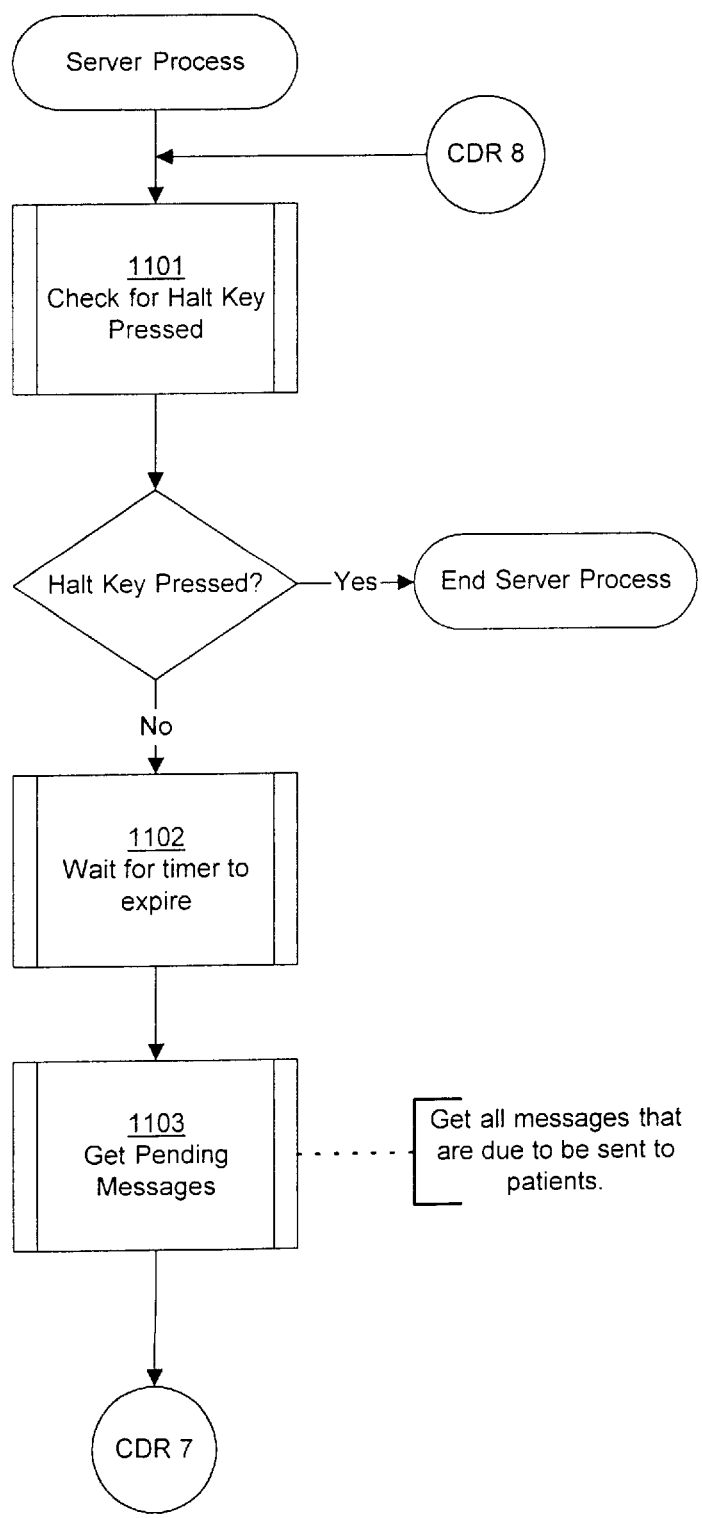
FIG. 4 is a schematic of a preferred embodiment of the computer software architecture utilized by the server system to forward to the patient messages relating to the patient's medical regimen.
Figure 4:
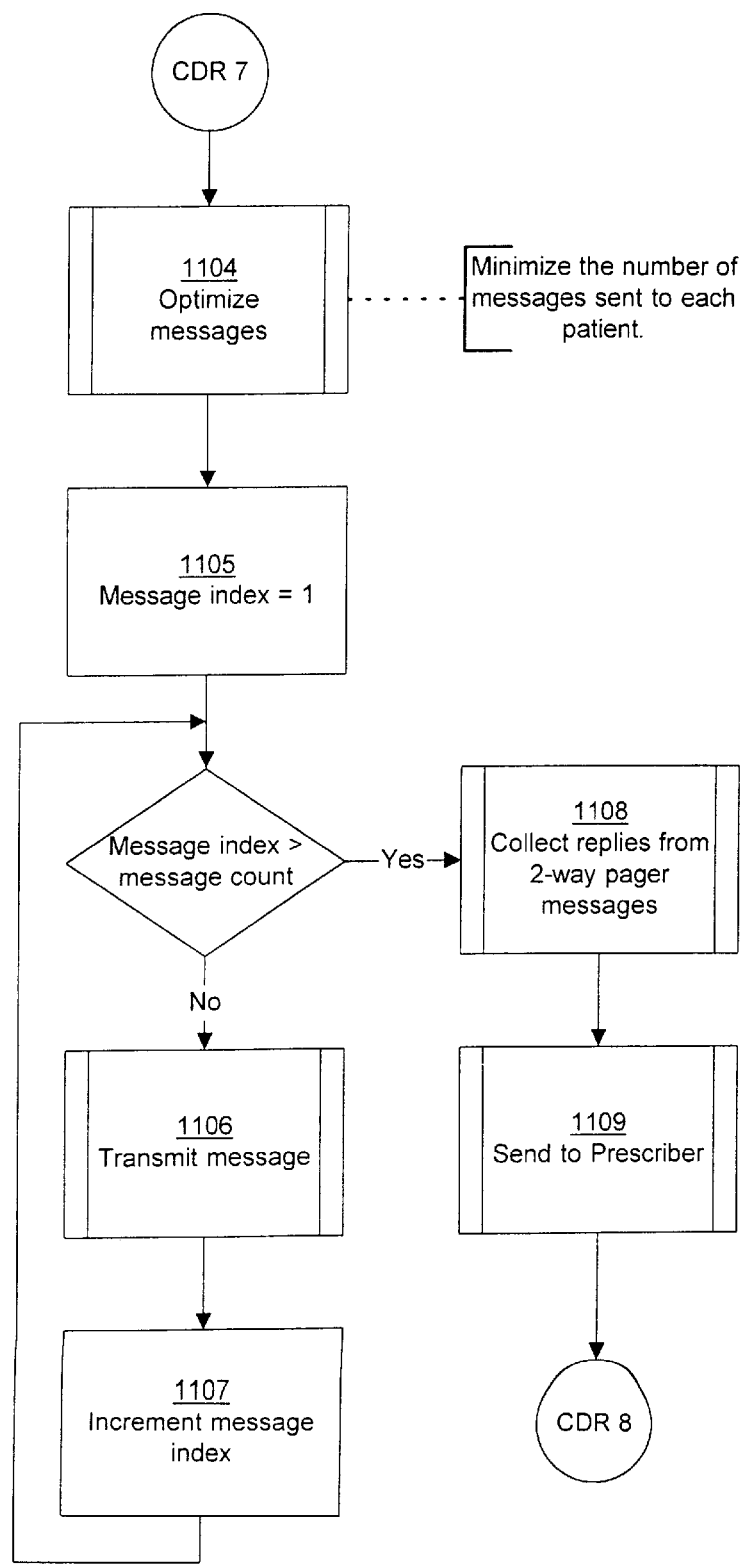

FIGS. 3 and 4 illustrate a preferred scheme using the prescriber computer system B and the server computer system A, respectively, to perform each of the steps involved in developing and monitoring a prescribed drug regimen. FIGS. 3A and 3B are preferred software subroutines used in the prescriber computer system B to check whether the prescribed drug is within the recommended dosage range and whether the prescribed drug creates any objectionable interaction with other drugs which the patient is taking, respectively. FIG. 3A-1 is a more preferred software subroutine within the dosage range check routine to determine if the prescribed drug regimen is within the recommended daily dosage range and within the recommended unit dosage. FIG. 3A-2 is a more preferred software subroutine to determine if in the standard medication mode, the total dosage is within the recommended duration range.

1. Inputting the pharmaceutical data. As one of the initial steps in preparing the system for use, pharmaceutical data will be inputted and stored in the server data storage unit 2. For each drug in the pharmaceutical data base, this data will include the prescription identification code (which will be found in the GPI or NDC identification codes), the GPI, the NDC and the KDC, the class of chemical components of the prescribed drug, the recommended unit dosage, the recommended standard daily dosage range, the recommended acute dosage range including the unit, daily, and prescribing duration acute ranges, the recommended maintenance unit, daily, and duration dosage range, and the recommended route, or routes, in which the drug is to be administered. This data is provided by the various pharmaceutical companies to the U.S. FDA which accumulates and distributes the information.

2. Inputting the patient and patient prescription data. The prescriber will in most cases, but not necessarily in all cases, be the patient's treating physician who desires to prescribe a particular medication to the patient to assist in the treatment of some medical illness. The prescriber computer station 7 is constructed to permit the prescriber to input into the system that patient data and patient prescription data necessary for the prescriber to ascertain that the dosage of the prescribed medication is within the recommended standard unit dosage, daily dosage or duration ranges, acute unit and daily dosage ranges, as well as the acute duration range; maintenance unit and daily dosage ranges, as well as the maintenance duration range, or if there is likely to be a drug—drug interaction, a drug-food interaction, a drug-alcohol interaction; or if there has been a prior adverse reaction by the patient to the particular drug or class of drugs being prescribed.

The patient prescription data will include the patient's identification code (e.g., social security number), the prescription GPI or NDC, the prescribed unit dosage, the prescribed daily dosage, the number of refills, the schedule of taking the prescribed drug, including time of first administration and frequency of administration, and the administering mode (i.e., standard, acute or maintenance mode). The patient prescription data will also include similar information for any other drug which the patient is currently taking. The patient prescription data can also include for each drug in the medical regimen the prescriber's name, the prescriber's practice name, address, and telephone number.

In a more preferred embodiment of the invention, it will also permit the inputting of patient data that will include the information necessary to expedite the delivery of the prescribed medication to the patient, to expedite the payment process for the prescribed medication, to generate patient messages to prompt the timely taking of the prescribed medication; and to continue to monitor the taking of the prescribed medication.

This patient data would include the patient's name, social security number, and address. It can also include the identification code of the pager assigned to the patient, as well as the name, address, telephone number, facsimile number, or identification number of the prescription delivery service D to be used to prepare and deliver the prescription. It can also include similar information regarding the entity, if other than the patient, who will pay part or all of the cost of the prescription. The patient data may also include medical history information relating to the patient, such as prior adverse reactions to specified drugs. It may also include such other information as patient height and weight, or any other general health information which the prescriber may believe beneficial in establishing a medical regimen for the patient.

Turning now to FIG. 3, in step 100, the prescriber logs into the software program and enters the patient's identification code. The preferred identification code will be the patient's social security number. The software will automatically connect the prescriber CPU 7 to the server CPU 1 through the use of modem 12 and modem 4. The server CPU 1 will search the patient data contained in the server data storage unit 2 to determine if previous patient data or patient prescription data had been entered regarding the particular patient in question. If so, this information is then transmitted to the prescriber CPU 7. If not, then in step 101 the prescriber will input through keyboard 9 the necessary patient and patient prescription data. The prescriber CPU 7 is further programmed to display the patient data on monitor 10 or, at prescriber's option, to print a hard copy of the patient data by use of printer 11. There is no preferred software to accomplish the above tasks. Any of the many commercially available data base and communication software programs can be used.

3. Assignment of Pager. As indicated above, one of the preferred embodiments of this invention is a reminder system which provides prior notification to the patient that certain of his prescribed medications should be administered. One of the problems with prior art systems is that patients are mobile. As a result many of the reminder messages are not timely received by the patient. Therefore, the preferred mode of communicating with the patient is by pager 14.

In a more preferred embodiment, the pager 14 will be a two-way pager which permits the patient to indicate receipt of the message. This system also permits the message to include not only a reminder to take the prescribed medication, but also to query the patient on other health matters, and to receive from the patient an updated status as to the health of the patient, the effectiveness of the prescribed medical regimen, or any health problems that may have arisen as a result of the prescribed medical regimen.

To effect this preferred mode, in step 200 the software program is structured to search the patient data located in the server storage unit 2 and the prescriber storage unit 8 to determine if a pager had been previously assigned to the patient. If no pager has been previously assigned to the patient, then in step 201 a pager is assigned by inputting the pager identification code into the patient data. This information is transmitted to the server computer system A which will in step 202 transmit a test message in accordance with the procedure described in FIG. 4 and discussed below.

4. Entering the patient prescription data. Upon verification that a pager has been assigned to the patient, the prescriber then inputs in step 300 through keyboard 9 that portion of the patient prescription data identified above that is necessary to verify that the prescription complies with a recommended dosage range, a recommended administering duration range, is free of adverse drug—drug reactions, drug-food reactions, drug-alcohol reactions, and known prior patient adverse drug reactions.

From this patient prescription data and the patient data, the prescriber CPU 7 is in step 400 programmed to generate a drug regimen that is then transmitted through modems 12 and 4 to the server CPU 1 for retention in the server data storage unit 2.

In a preferred embodiment, the prescriber will indicate if information identifying the drug being prescribed is to be made available to other prescribers. This embodiment permits the prescriber to maintain certain information confidential and be disseminated on a need-to-know basis. This is achieved by designating at step 500 the drug description as confidential. Although a drug has been designated as confidential, the system is preferably designed to still perform the dosage range check, the drug interaction checks, and the prior patient adverse drug reactions check. Thus, another prescriber will know if the unidentified drug causes any problem with a drug which the prescriber may wish to administer. In this circumstance, a message providing the prescriber's name and telephone number will be entered into the patient data. When the patient data is subsequently recalled, another prescriber will thus have the ability to contact the originating prescriber and determine the identity of the prescription.

In another preferred embodiment, the prescriber can indicate if the drug being prescribed is an experimental drug. This is also achieved in step 500 by designating the drug as experimental. However, in this event there is no further drug dosage check or drug interaction check, as there will not be sufficient information in the data bases to make those determinations.

5. Prescribed Dosage Check Procedure. Upon the transmittal of the drug regimen to the server data storage unit 2, the prescriber CPU 7 is programmed in step 600 to request that the server CPU 1 retrieve from the server data storage unit 2 the pharmaceutical data relating to each of the prescriptions contained in the schedule, as well as to each of the other prescriptions which the patient is currently taking. With this information, and as further described in FIG. 3A, the prescriber CPU 7 is programmed to check each prescription to determine if it is within the recommended unit dosage range or the recommended daily dosage range, as well as within the recommended medicating duration range for the prescribing mode; i.e., standard, acute, or maintenance. In a preferred embodiment, the program is constructed to default to a standard dosage mode. However, if the prescriber had indicated that the drug regimen has been set for a maintenance or acute dosage, then as detailed below in FIG. 3A, each such prescription is checked to determine if it is within the recommended maintenance dosage ranges or the recommended acute dosage range, whichever may be indicated.

If the prescription is not within the recommended ranges, then the prescriber CPU 7 is programmed to display this information on the prescriber monitor 10 where the prescriber is directed to amend the prescription to be within the recommended ranges.

(a) Dosage and Duration Range Check

FIGS. 3A, 3A-1, and 3A-2 provide a preferred software routine for the method of conducting a comparison of the patient data and the patient prescription data to the associated pharmaceutical data to determine if there are any deviations from recommended dosage or duration ranges.

In addition, the prescriber CPU 7 has been programmed to transmit its determinations to prescriber monitor 10 and printer 11. Also, along with the determinations, suggested actions may be provided to the prescriber. Although the language used, as well as the content of the determinations and suggested actions may vary within the scope of the invention, the following would be exemplary of the messages provided to the prescriber or physician:

| MESSAGE NUMBER | MESSAGE DESCRIPTION |
|---|---|
| 1 | Adult Dose Checking is not Available. |
| 2 | Geriatric Dose range checking is not available. Comparison to normal adult dosing may or may not be appropriate. |
| 3 | Pediatric Dose Range Checking is not available. Consult a pediatric dosing reference is recommended. |
| 4 | Infant Dose Checking is not available. Consult a pediatric dosing reference is recommended. |
| 5 | This dose falls below the recommended daily dose for this drug and is potentially subtherapeutic. |
| 6 | This dose falls above the recommended daily dose for this drug. Please verify this daily dose. |
| 7 | This dose falls above the recommended maximum individual dose for this drug. Please verify the dosage regimen. |
| 8 | No further information available. |
| 9 | This dose falls below the recommended maintenance dosage range for this drug and is potentially subtherapeutic. |

-continued

| MESSAGE NUMBER | MESSAGE DESCRIPTION |
|---|---|
| 10 | This dose falls above the recommended maintenance dosage range for this drug. Please verify this daily dose. |
| 11 | This dose falls below the recommended acute dosage range for this drug and is potentially subtherapeutic. |
| 12 | This dose falls above the recommended acute for this drug. Please verify this daily dose. |
| 13 | The duration of therapy falls below the recommended duration of therapy range for acute dosing and is potentially ineffective. |
| 14 | The duration of therapy exceeds the recommended duration of therapy range for acute dosing of this drug. Please verify the prescribed length of acute therapy. |
| 15 | Minimum Duration of Therapy is not available. |
| 16 | Maximum Duration of Therapy is not available. |
| 17 | The duration of therapy falls below the recommended duration of therapy range and is potentially ineffective. |
| 18 | The duration of therapy exceeds the recommended duration of therapy range for this drug. Please verify the prescribed length of therapy for this drug. |

When these messages are preferably transmitted is set forth below.

The first step 601 is to calculate the age of the patient from the information in the patient data. If this information is not in existing patient data, then the prescriber will input in the necessary information to calculate the age of the patient.

Recommended dosage ranges may vary depending on the age of the patient. Currently, dosage ranges have been defined for infants (ages of 0–1), adolescents (ages of 1–14), adults (ages 14–65) and geriatrics (ages >65). This age division is used by the system to provide dosage range checks. Obviously, if these current divisions change, then the software program could be easily modified to accommodate such changes.

Next, in step 602, the prescriber central processing unit 7 is programmed to determine if the patient age is 65 or greater. Then the GPI or NDC is read at step 603. If the GPI or NDC is not stored in the server data storage unit 2, prescriber central processing unit 7 will perform step 604 to transmit to prescriber report unit 10 a message that geriatric dose range checking is not available. The message may also provide guidance to the prescriber, such as comparison to normal adult dosing may or may not be appropriate (Message Number 2). The prescriber CPU 7 is then further programmed to begin at step 612, described below, to check to determine if there is a prescription identification number included within the adult dosage category. If the GPI or NDC is stored in the server data storage unit 2, then the prescribed dosage and the recommended adult dosage range are compared in step 605 to determine if the prescribed dosage is within the recommended adult dosage range.

(i) Dosage Range Check. Step 605 is set forth in more detail in FIG. 3A-1. In the first step 605A the prescriber CPU 7 is programmed to calculate a DoseUnit (daily dosage). This is obtained by dividing the total drug quantity by the prescribed duration. In step 605B the prescriber CPU 7 is programmed to calculate an IndividualDose (unit dosage). This is obtained by dividing the DoseUnit by the frequency a patient is to take the medication. Next, in step 605C a comparison is made by the prescriber CPU 7 between the prescribed daily dosage and the recommended minimum daily dosage. If the prescribed daily dosage is less than the minimum recommended daily dosage, prescriber CPU 7 is programmed in step 605D to generate a message for transmission to the prescriber monitor 10 and then proceed to step 605E. The message would indicate that the prescribed daily dosage is less than any dosage in the recommended total daily dosage range and that the prescribed dosage is potentially subtherapeutic (see Message Number 5). However, if the prescribed daily dosage is greater than the recommended minimum daily dosage, the prescriber CPU 7 is programmed in step 605E to compare the prescribed daily dosage to the recommended maximum daily dosage. If the prescribed daily dosage is greater than the recommended maximum daily dosage, then the prescriber CPU 7 is programmed in step 605F to generate a message for transmission to the prescriber monitor 10 and then proceed to step 605G. The message would indicate that the prescribed dosage falls above the recommended daily dose for the drug, and requests the prescriber to verify the prescribed daily dose (See Message Number 6). If the prescribed daily dosage is less than the maximum daily recommended dosage, then the prescriber CPU 7 in step 605G compares the prescribed unit dosage to the recommended maximum unit dosage. If the prescribed individual dosage is greater than the recommended maximum unit dosage, prescriber CPU 7 is programmed in step 605H to generate a message for transmission to prescriber monitor 10 that the prescribed dosage falls above the recommended unit dosage for the drug, and requests the prescriber to verify the prescribed dosage regimen (See Message Number 7) and to proceed to the maintenance mode range check at step 615. If the prescribed unit dosage is below the recommended unit dosage, then prescriber CPU 7 is programmed as described below to determine if the prescribed dosage is within the mode ranges being prescribed.

Returning now to FIG. 3A, if the age of the patient is less than 65, but determined in step 606 to be less than 14 years, then, in step 607, it is determined if the age of the patient is greater than one year. If not, then, in step 608, prescriber CPU 7 is programmed to generate a message that infant dose checking is not available. It may also recommend that the prescriber consult a pediatric dosing reference (See Message Number 4). Once the message has been transmitted, the prescriber CPU 7 is programmed to terminate the dosage check subroutine and proceed to the drug interaction check subroutine. If the age of the patient is determined to be between 14 years and one year, then, in step 609, the GPI or NDC is read from the prescription data. If, in step 610, no matching GPI or NDC can be located in server data storage unit 2, then prescriber CPU 7 is programmed in step 611 to generate a message that pediatric dose range checking is not available. The message may recommend that the prescriber consult a pediatric dosing reference (See Message Number 3). Once the message has been transmitted, the prescriber CPU 7 is programmed to terminate the dosage check subroutine and to proceed to the drug interaction check subroutine. However, if a GPI or KDC is located in step 610, then prescriber CPU 7 is programmed to perform step 605 previously described.

If, in step 606, the age of the patient is determined to be between 15 years and 65, then, in step 612, the GPI in the prescription data is read by the prescriber CPU 7 and compared in step 613 to the GPI's stored in server data storage unit 2 to determine if pharmaceutical data is stored in the server data storage unit 2 corresponding to the GPI. If not, then, in step 614, prescriber CPU 7 is programmed to generate a message that adult dosage checking is not available (See Message Number 1). After the message has been transmitted, prescriber CPU 7 is programmed to end the dosage range check and to begin the drug interaction check subroutine at step 700. If the pharmaceutical data corresponding to the GPI is located in the server data storage unit 2, in step 613, the prescriber CPU 7 is programmed to begin Dose Range Check step 605. In a preferred embodiment the DNC will contain a corresponding GPI designation for each drug in the DNC. Thus, if the prescriber inputs DNC designations into the prescriber CPU 7, the software is designed to located the corresponding GPI designation and then to utilize the GPI designation to obtain the necessary data to perform the checks.

In step 615, prescriber CPU 7 is programmed to determine if the patient prescription data indicates that the prescription dosage is a maintenance dosage. If so, then prescriber CPU 7 is programmed to determine if the prescription dosage is within associated recommended maintenance dosage ranges. In step 616, it is determined if the prescription dosage is greater than the maximum maintenance dosage in the recommended maintenance dosage range. If not, then, in step 617, it is determined if the prescription dosage is less than the minimum maintenance dosage in the recommended maintenance dosage range. If it is, then, in step 618, the prescriber CPU 7 is programmed to generate a message that the dosage falls below the recommended maintenance dosage range for this drug and is potentially subtherapeutic. (See Message Number 9) If in step 617 the prescribed dosage is greater than the recommended minimum maintenance dosage, then the prescriber CPU 7 is programmed to conclude the dosage check subroutine and to proceed with the drug interaction check subroutine.

If in step 616 the prescribed dosage is greater than the recommended maximum maintenance dosage, then in step 619 the prescriber CPU 7 is programmed to search to determine if an acute dosage record exists. If no record can be found, then in step 620 the prescriber CPU 7 is programmed to generate and transmit to prescriber monitor 10 a message that the prescribed dosage falls above the recommended maintenance dosage range for the drug, and requests the prescriber to verify the daily prescribed dosage. (See Message Number 10) Upon transmission of the message, the prescriber CPU 7 is programmed to terminate the dosage check subroutine and to proceed with the drug interaction check subroutine.

If the prescription data indicates that the dosage prescribed is an acute dosage, then in step 621, the prescribed dosage is checked to determine if it is within the recommended acute dosage range associated with that prescription. If the prescribed dosage exceeded the maximum acute dosage range, then, in step 622, the prescriber CPU 7 is programmed to generate a message that the dose falls above the recommended maximum acute dosage for this drug. The message can include suggestions to the prescriber such as requesting the prescriber to verify the daily dosage. (See Message Number 12) Upon transmission of the message, the prescriber CPU 7 is programmed to begin the drug interaction check subroutine. If the prescribed dosage is not greater than the maximum acute dosage in the recommended acute dosage range, then, in step 623, it is determined if the prescribed dosage is less than the minimum acute dosage in the recommended acute dosage range. If it is, then, in step 624, the prescriber CPU 7 is programmed to generate a message that the prescription dosage falls below the recommended acute dosage range for this medication and is potentially subtherapeutic. (See Message Number 11) Upon transmission of the message, the prescriber CPU 7 is programmed to begin the drug interaction check subroutine. However, if the prescription dosage is not less than the minimum acute dosage in the recommended acute dosage range, then, in step 625 the prescriber CPU 7 is programmed to calculate the prescribing duration for the drug being checked. The prescribing duration is determined by dividing the total quantity prescribed by the daily quantity prescribed. Then with the calculated prescribing duration, prescriber CPU 7 is programmed to determine in step 626 if the prescribing duration period is greater than the maximum acute duration period in the recommended acute duration period range. If the prescribing duration period is greater, then, in step 627, the prescriber CPU 7 is programmed to generate a message that the duration of therapy exceeds the recommended duration of therapy range for acute dosing of this drug. It may also suggest that the prescriber verify the prescribed length of acute therapy. (See Message Number 14) If the prescription duration period is less than the maximum duration period in the recommended duration period range, then, in step 628, it is determined if the prescription duration period is less than the minimum duration period in the recommended duration period range. If not, then the prescriber CPU 7 is programmed to terminate the drug dosage check and to proceed to the drug interaction check subroutine. However, if the prescription duration period is less than the minimum recommended duration period, then, in step 629, prescriber CPU 7 is programmed to generate a message that the duration of therapy falls below the recommended duration of therapy range for acute dosing and is potentially ineffective. (See Message Number 13) Upon transmission of the message, the prescriber CPU 7 is programmed to begin the drug interaction subroutine.

If the prescription is not a maintenance mode dosage or if no maintenance record can be located in step 615, then prescriber CPU 7 is programmed to determine in step 630 whether an acute mode record exists. If an acute mode record exists, then prescriber CPU 7 is programmed to begin step 621 as described above. If no acute mode record exists, then prescriber CPU 7 is programmed to begin in step 631 the drug prescribing duration check subroutine.

(ii) Prescribing Duration Check. Referring now to FIG. 3A-2, prescriber CPU 7 is programmed to calculate the prescribing duration for each new drug to be prescribed in a medical regimen. This step 631A is substantially the same as step 625. Prescriber CPU 7 is then programmed to search in step 631B the pharmaceutical data to determine if there is a recommended minimum prescribing duration period for the drug being checked. If none is found, then prescriber CPU 7 is programmed to generate and transmit to monitor 10 in step 631C a message, and then to proceed to step 631 D. The message would indicate that there is no recommended minimum prescribing duration (See Message Number 15).

Prescriber CPU 7 is programmed to then search the pharmaceutical data to determine in step 631D if there is a recommended maximum prescribing duration. If none is found, the prescriber CPU 7 is programmed to generate and transmit to monitor 10 in step 631E a message, and then proceed to step 631F. The message would indicate that there is not a recommended maximum prescribing duration (See Message Number 16).

If a recommended minimum prescribing duration was found in step 631F, then prescriber CPU 7 is programmed to determine in step 631F if the calculated prescribing duration is less than the recommended minimum. If so, then prescriber CPU 7 is programmed to generate and transmit to monitor 10 in step 631G a message to this effect (See Message Number 17). The prescriber CPU 7 is also programmed after sending the message to proceed to step 631H. Similarly, in steps 631H and 631I, prescriber CPU 7 is programmed to determine if the calculated prescribing duration is greater than the recommended prescribing duration for the drug being checked. If so, a message to this effect (See Message Number 18) is generated and transmitted to Monitor 10.

6. Drug Interaction Checking Procedure. Prescriber CPU 7 is next programmed in step 700, as referenced in FIG. 3 and 3B, to retrieve from the previously transmitted pharmaceutical data now stored in the server data storage unit 2 the information necessary to determine if any of the drugs included within the medical regimen will cause an unacceptable reaction with any other drug included within the medical regimen. The preferred subroutine is illustrated in FIG. 3B.

In step 701, the prescriber CPU 7 is programmed to create an empty interaction list. Next, in step 702, the prescriber CPU 7 is programmed to compare the GPI of a prescribed drug with the NDC stored in the server data storage unit 2 in order to collate the GPI with the corresponding NDC to locate the KDC. If in step 703, the corresponding KDC is located, then in step 704 the KDC is retained by the prescriber CPU 7. The prescriber CPU 7 is programmed in step 705 to include the finding in a final report. If the KDC in step 703 was not found, then the prescriber CPU 7 is programmed to retain that finding. In the next step 707, prescriber CPU 7 searches the pharmaceutical data to look for the drug formulation record (containing the compound classes which the drug contains) for each drug in the medical regimen. If at step 708 the record is found, then prescriber CPU 7 is programmed at step 709 to create a list of classes that each drug in the medical regimen would be classified, and at step 710 to retain the finding. If at step 708 no drug formulation record could be found, then prescriber CPU 7 is programmed to retain at step 711 this finding. The prescriber CPU 7 is programmed to compare the classes of each drug in the medical regimen to determine at step 712 if there would be any anticipated unacceptable drug interactions because of the compound classes in which a drug may be included. Any unacceptable drug interactions located are accumulated in a list at step 713. If there are unacceptable drug interactions included in the list, then the prescriber CPU 7 is programmed to generate and then instruct prescriber printer 11 in step 714 to print the findings of the drug interaction test or display on monitor 10 these findings. The prescriber may then modify the drugs being prescribed to eliminate the unacceptable drug interactions. If there are no unacceptable drug interactions, the prescriber CPU 7 is programmed to end the drug interaction check subroutine and to proceed to step 800 to check for prior patient reactions to any drug being prescribed in the medical regimen.

If there are unacceptable reactions between drugs included within the medical regimen, the prescriber CPU 7 is programmed to display this information on the prescriber monitor 10. The prescriber then modifies one or more of the drugs to eliminate the unacceptable reaction. The new prescriptions are then checked for compliance with both the dosage and duration ranges, as well as for unacceptable drug interactions. This procedure is repeated until the prescribed medical regimen meets the recommended standards.

7. Prior Drug Reaction Checking Procedure. Once the prescribed medical regimen is within the recommended dosage and duration ranges and there are no unacceptable drug interactions, the prescriber CPU 7 is programmed in step 800 to search the patient data to determine if the patient has ever reported any adverse reaction to any of the drugs, or classes of drugs, in the prescribed medical regimen.

If so, the prescriber CPU 7 is programmed to display this information on the prescriber monitor 10. The prescriber then modifies the prescribed medical regimen to eliminate the unacceptable known reaction. The modified regimen is then again checked for dosage, administering duration, drug interaction, and prior known drug reactions. The procedure is repeated until the prescribed medical regimen meets all of the recommended dosage and duration range requirements, and there is no unacceptable drug interaction and drug reactions.

8. Report Generation Procedure. Once the medical regimen has been set, the prescriber CPU 7 is programmed in step 900 to direct prescriber printer 11 to print for the patient, the prescription calendar and prescribed medical regimen for the patient to follow. The prescriber CPU 7 is further programmed in step 1000 to transmit the final prescribed medical regimen to the server CPU 1 for storage into the server data storage unit 2.

In a preferred embodiment, the prescriber will be able to send to the patient more than prescription messages, such as appointment reminders or refill reminders. In addition these messages could include instructions on how to take the medication, how to conduct various medical procedures (e.g., how to clean a wound, etc.), or combinations of both. In this embodiment after step 900, the prescriber CPU 7 asks the computer operator whether there are any non-prescription messages. If not, then the prescriber CPU 7 is programmed to proceed to step 1000 described above. If there are non-prescription messages, then the prescriber CPU 7 is programmed to receive in step 901 the message inputted by prescriber keyboard 9. Once the message has been inputted, the prescriber CPU 7 is programmed to produce in step 902 a schedule of non-prescription messages. After the schedule has been produced, the prescriber CPU 7 is programmed to proceed to step 1000 described above.

The Method of Utilizing the System for Patient Compliance

In the preferred embodiment, server computer station A is utilized to transmit messages to the patient. These messages will include prior notification of when and what medications the patient is scheduled to take in accordance with the prescribed medical regimen. The server CPU 1 is programmed to operate in accordance with the procedure illustrated in FIG. 4.

Server CPU 1 is programmed in step 1101 to first determine if it has received a command to stop further processing. This command is given if a fault in the system hardware or software has occurred, or if stoppage of the system is desired by the operator for any reason. If no halt command has been received, server CPU 1 is programmed in step 1102 to perform no message delivery function for a predetermined period of time. This period is to allow the prescriber to more easily and quickly access the CPU 1 to retrieve patient prescription data or pharmaceutical data, as well as to make and enter into the server data storage unit 2, any changes to the patient prescription data. This feature becomes more important as greater number of prescribers are connected to the server CPU 1. A preferred period of time is 30 to 60 seconds. Upon the lapse of the delay period, server CPU 1 is programmed in step 1103 to retrieve any messages that are scheduled to be transmitted within an upcoming time period. These messages are sorted by delivery time. In the event a patient has more than one message, the server CPU 1 is programmed in step 1104 to combine all of these messages into a single message for transmission to the patient.

In step 1105, the number of messages is counted. If the number of messages is greater than one, the server CPU 1 is programmed in step 1106 to transmit through modem 5 the first message to the appropriate patient message receiving unit 13. Step 1106 is repeated until all of the messages identified in step 1105 have been transmitted. This process is continued until there are no remaining messages to be transmitted. The server CPU 1 is then programmed to again determine if a halt command has been received. The procedure is then continued as before.

The patient message receiving unit 13 upon receiving a message is activated to call the patient's pager and deliver the message. If the pager 14 is a two-way pager, the patient will have been instructed to acknowledge receipt of the message. If the message is more than notification to take medication, the patient can also respond to any queries that may be included in the message. In this event, the server CPU 1 is programmed to search at step 1108 for these reply messages when the message count if greater than one. The collected messages are then transmitted at step 1109 to be processed by the server. There are of course many alternative procedures for routing the patient's response to the prescriber. For example, patient message receiving unit 13 may be directly connected to prescriber modem 12. In another alternative route, modem 5 can be directly connected to prescriber modem 12.

The Method of Utilizing the System for Prescription Delivery

In this embodiment, the prescriber CPU 7 is programmed to transmit, via prescriber modem 12, the patient prescriptions to the server CPU 1. The server CPU 1 is also programmed to transmit using commercially available communications software these patient prescriptions to the prescription delivery system D.

Prescription delivery system CPU 18 is programmed to retrieve drug cost data stored in its data storage units. This data is then collated to the drugs contained in the prescriptions in order to generate an invoice and other desired documentation which is then produced by printing unit 19 to be included with the prescriptions when delivered to the patient.

The Method of Utilizing the System for Prescription Payment

If the patient will be the person paying for the prescriptions, then the invoice generated by the prescription delivery system D will be delivered to the patient.

If the payor is to be an insurance company, HMO, other health maintenance provider, or government agency, the invoice generated by the prescription delivery system D will be delivered, preferably modemed, to the payor system E for payment. In an alternate preferred embodiment, the invoice delivery could be conducted electronically or optically. In this embodiment the invoice will be transmitted through server computer station A to payor system E. This can be achieved through any number of readily available commercial communications software programs. In another alternate preferred embodiment, the prescription delivery system D will directly communicate by well known linked computer systems to payor system E.

A copy of a preferred software program for use with the system and method of this invention is set forth in Exhibit 1.

There are of course other alternate embodiments which are obvious from the foregoing descriptions of the invention which are intended to be included within the scope of the invention as defined by the following claims.

What I claim is:

1. A system to facilitate compliance with a prescribed medical regimen comprising:
    (a) a computer system having a data storage unit capable of storing patient data and patient prescription data;
    (b) a central processing unit programmed and operatively connected to said data storage unit to store said patient data and said patient prescription data in said data storage unit;
    (c) wherein said system includes a program stored in said central processing unit to generate and transmit from a patient prescription a patient message, wherein said patient message includes a drug and a dosage to be administered by a patient at a time of receiving said patient message in order that said patient complies with said patient prescription;
    (d) a message receiving unit operatively connected to said central processing unit to receive said patient message from said central processing unit;
    (e) a message transmitting unit operatively connected to said message receiving unit and transmitting said patient message at a time proximate to when said patient is scheduled to administer a unit dosage; and
    (f) a pager allowing said patient to receive said patient message transmitted from said transmitting unit.

2. A system according to claim 1, wherein said program allows said central processing unit to enter patient prescription data into said data storage unit from a separate computer system of a prescribing physician.

3. A system according to claim 1, wherein:
    (a) said data storage unit is further capable of storing pharmaceutical data; and
    (b) said program stored in said central processing unit allows comparison of said patient prescription data to said patient data and said pharmaceutical data to determine if said patient prescription data is within recommended daily and unit dosage ranges.

4. A system according to claim 3, wherein said program stored in said central processing unit:
    (a) allows comparison of said patient data and patient prescription data to determine if said patient prescription data is within a recommended prescribing duration range as defined by said pharmaceutical data; and
    (b) transmits the determination to a reporting unit.

5. A system according to claim 3, wherein:
    (a) said system includes a program to generate and transmit a prescription invoice; and
    (b) said system further comprises a payment system operatively connected to said central processing unit to receive said prescription invoice.

6. A system according to claim 3, wherein said determination of whether said patient prescription data is within said recommended daily and unit dosage ranges is transmitted to a reporting unit.

7. A system according to claim 1 wherein:
    (a) said patient data comprises:
        (i) a patient identification code used to identify said patient,
        (ii) data necessary to determine age of said patient, and
        (iii) a listing of other medications which said patient may be taking; and (b) said patient prescription data comprises:
  (i) a prescription identification code used to identify a medication to be prescribed,
  (ii) a prescription dosage of said medication to be used in said medical regimen,
  (iii) a duration period of taking said medication to be used in said medical regimen, and
  (iv) a frequency schedule of taking a prescribed amount of said dosage in said medical regimen.

8. A system according to claim 1 wherein said data storage unit is further capable of storing pharmaceutical data and said pharmaceutical data comprises:
  (i) a listing of identification codes used to identify medications,
  (ii) for each medication in said listing, a recommended dosage range, a recommended duration range, a maintenance dosage range, and an acute dosage range, and
  (iii) for each medication contained in said listing, known interactions of each of said medications with other medications contained in said listing.

9. A system according to claim 1, wherein:
  (a) said data storage unit is further capable of storing pharmaceutical data; and
  (b) said program stored in said central processing unit:
    (i) allows comparison of said patient data and patient prescription data to determine if said patient prescription data is within a recommended prescribing duration range as defined by said pharmaceutical data; and
    (ii) transmits the determination to a reporting unit.

10. A system according to claim 1 wherein:
  (a) said data storage unit is further capable of storing pharmaceutical data; and
  (b) said program:
    (i) compares said patient prescription data to said pharmaceutical data to determine if said drug to be prescribed has one or more known drug interactions with other medication said patient is taking; and
    (ii) transmits a report to a prescribing physician if a known drug interactions exist.

11. A system according to claim 10, wherein said program:
  (a) amends said patient prescription data to eliminate said drug interaction if a known drug interactions exist; and
  (b) transmits said amended prescription data to said central processing unit.

12. A system according to claim 1, wherein:
  (a) said system includes a program to generate and transmit a prescription invoice; and
  (b) said system further comprises a payment system operatively connected to said central processing unit to receive said prescription invoice.

13. A system according to claim 1 wherein said message receiving unit comprises a modem operatively connected to said transmitting unit to transmit said patient message to said pager.

14. A system according to claim 1, wherein said pager is a two way pager.

15. A system according to claim 1, wherein said system further includes:
  (a) pharmaceutical data stored in said data storage unit; and
  (b) said program further:
    (i) compares said patient prescription data to said pharmaceutical data to determine if said patient prescription data indicates that unacceptable drug interactions will occur from the drugs included within said medical regimen; and
    (ii) transmits the determination to a reporting unit.

16. A system according to claim 1, wherein said system further includes a program to:
  (a) compare said patient prescription data to said patient data to determine if there were reported prior drug reactions to any of the drugs included within said medical regimen, and
  (b) transmit the determination to a reporting unit.

17. A system according to claim 1, wherein:
  (a) said data storage unit is further capable of storing pharmaceutical data, including a recommended dosage range for at least some of the drug included in said pharmaceutical data; and
  (b) said program determines if said dosage is within said recommended dosage range and transmits the determination to a reporting unit.

18. A system according to claim 17 wherein if said program determines said dosage is not within said recommended dosage range, said program:
  (a) amends said dosage to be within said recommended dosage range;
  (b) transmits said amended dosage to said central processing unit for storage in said data storage unit;
  (c) retrieves from said data storage unit said amended dosage prior to the time said patient is to administer said drug; and
  (d) notifies said patient as to when and how much of said drug to administer.

19. A method to facilitate compliance by a patient with a medical regimen prescribed by a prescriber utilizing a system including a computer station having a data storage unit containing stored pharmaceutical data, a central processing unit programmed and operatively connected to said data storage unit to further store patient data and patient prescription data in said data storage unit, an inputting unit operatively connected to said central processing unit to transmit to said central processing unit that portion of said patient data and patient prescription data necessary to determine if said patient prescription data is within an acceptable medication dosage range as defined by said portion of said pharmaceutical data, a reporting unit operatively connected to said central processing unit, and wherein said central processing unit being further programmed to compare said patient prescription data to said portion of said patient data and said pharmaceutical data to determine if said patient prescription data is within said acceptable medication dosage range, and to transmit the determination to said reporting unit, which comprises:
  (a) inputting into said central processing unit said patient data which comprises;
    (i) a patient identification code used to identify said patient,
    (ii) data necessary to determine age of said patient, and
    (iii) a listing of other medications which said patient may be taking;
  (b) inputting into said central processing unit said patient prescription data which comprises:
    (i) a prescription identification code used to identify a medication to be prescribed,
    (ii) a prescription dosage of said medication to be used in said medical regimen,
    (iii) a duration period of taking said medication to be used in said medical regimen, and (iv) a frequency schedule of taking a prescribed amount of said dosage in said medical regimen to said patient; and (c) inputting into said central processing unit said pharmaceutical data which comprises:
  (i) a listing of identification codes used to identify medications,
  (ii) for each medication in said listing, a recommended dosage range, a recommended duration period range, a maintenance dosage range, and an acute dosage range, and
  (iii) for each medication contained in said listing, known interactions of each of said medications with other medications contained in said listing; and (d) said comparing comprises the steps of:
  (i) reviewing said pharmaceutical data to determine if a prescription identification code exists for said medication,
  (ii) if no prescription identification code of said medication exists, then transmitting to said prescriber report unit that no prescription identification code for said medication exists in said pharmaceutical data,
  (iii) if a prescription identification of said medication exists, then from said patient data, from said pharmaceutical data, and from said patient prescription data, and using said central processing unit, compare said recommended dosage range to said prescription dosage to determine if said prescription dosage is within said recommended dosage range,
  (iv) if said prescribed dosage is not within said recommended dosage range, then from said patient data, said pharmaceutical data, and said patient prescription data, determine, using said central processing unit, if said prescribed dosage is within said recommended maintenance dosage,
  (v) if said prescribed dosage is not within said recommended dosage range, and if said prescribed dosage is not within said recommended maintenance dosage range, then from said patient data, said pharmaceutical data, and said patient prescription data, determine, using said central processing unit, if said prescribed dosage is within said recommended acute dosage range,
  (vi) from said patient data, from said pharmaceutical data, and from said patient prescription data, using said central processing unit, compare said duration period range to said prescribed duration period to determine if said prescribed duration period is within said recommended duration period range; and (e) transmitting the determination to said reporting unit.

20. A method according to claim 19 further comprising transmitting to said prescriber report unit the determinations of the comparisons made between said recommended dosage range and said prescribed dosage and between said recommended duration period range and said prescribed duration period.

* * * * *